(12) United States Patent
Beavis

(10) Patent No.: US 6,399,855 B1
(45) Date of Patent: Jun. 4, 2002

(54) QTL MAPPING IN PLANT BREEDING POPULATIONS

(75) Inventor: William D. Beavis, Rio Rancho, NM (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/216,089

(22) Filed: Dec. 18, 1998

Related U.S. Application Data

(60) Provisional application No. 60/068,822, filed on Dec. 22, 1997, and provisional application No. 60/084,048, filed on May 4, 1998.

(51) Int. Cl.$^7$ .............................. A01H 5/00; C12N 5/04
(52) U.S. Cl. ...................... 800/266; 800/267; 800/278
(58) Field of Search ................................. 800/266, 267, 800/275

(56) References Cited

U.S. PATENT DOCUMENTS

| | | | |
|---|---|---|---|
| 5,412,087 A | 5/1995 | McGall et al. | |
| 5,437,697 A | 8/1995 | Sebastian et al. | |
| 5,492,547 A | 2/1996 | Johnson | |
| 5,571,639 A | 11/1996 | Hubbell et al. | |

FOREIGN PATENT DOCUMENTS

| | | |
|---|---|---|
| WO | WO89/07647 | 8/1989 |
| WO | WO95/20669 | 8/1995 |

OTHER PUBLICATIONS

International Preliminary Examination Report for PCT/US98/26934, dated Jan. 26, 2000.

Bubeck et al., (1993) Quantitative trait loci controlling resistance to gray leaf spot in maize. *Crop Science* 33(4):838–847.

Doebley et al., (1996) Mapping the genes that made maize. *Trends in Genetics*: 882–896.

Austin et al., (1996) Genetic resolution and verification of quantitative trait loci for flowering and plant height with recombinant inbred lines of maize. *Genome* 39:957–968.

Beavis et al., (1994) Identification of quantitative trait loci using a small sample of topcrossed progeny for maize. *Crop Science* 34(4):882–896.

Jansen, Ritsert. (1996) Complex plant traits: time for polygenic analysis. *Trends in Plant Science* 1(3):89–94.

Beavis, William B. (1998) QTL Analyses: Power, Precision, and Accuracy. *Molecular Dissection of Complex Traits*:145–162.

Xu et al., (1995) A Random Model Approach to Interval Mapping of Quantitative Trait Loci. *Genetics* 141:1189–1197.

Van Arendonk et al. (1994) Use of Multiple Genetic Markers in Prediction of Breeding Values. *Genetics* 137:319–329.

*Primary Examiner*—Gary Benzion
(74) *Attorney, Agent, or Firm*—Jonathan A. Quine; Gwynedd Warren

(57) ABSTRACT

This invention relates to a method for improving the efficacy of a plant breeding program by selectively altering the average of a quantitative phenotypic trait in a plant population. The method employs statistical models to predict the association of genetic markers with a desired phenotypic trait. These models allow the association to be extrapolated to the progeny of the plants tested as well as plants in other families within the breeding population. After the statistical association has been determined, the genetic markers which associate with quantitative trait loci can be used to screen for plants with the desired genetic markers to use as progenitors of an F1 seed population. Alternatively, after the alleles which associate with a QTL have been identified, the coding sequences of at least one of the alleles can be cloned and introduced into a plant to create a transgenic plant line.

34 Claims, No Drawings

QTL MAPPING IN PLANT BREEDING POPULATIONS

CROSS-REFERENCES TO RELATED APPLICATIONS

This Patent Application is related to U.S. Provisional Patent Application Nos. 60/068,822, filed Dec. 22, 1997 and 60/084,048, filed May 4, 1998. Both of these priority documents are incorporated by reference in their entirety.

STATEMENT AS TO RIGHTS TO INVENTIONS MADE UNDER FEDERALLY SPONSORED RESEARCH AND DEVELOPMENT

Not applicable.

BACKGROUND OF THE INVENTION

Historically, the term "quantitative trait" has been used to describe variability in expression of a phenotypic trait that shows continuous variability and is the net result of multiple genetic loci possibly interacting with each other and/or with the environment. To describe a broader phenomenon, the term "complex trait" has been used to describe any trait that does not exhibit classic Mendelian inheritance attributable to a single genetic locus (Lander & Schork, *Science* 265:2037 (1994)). The distinction between the terms, for purposes of this disclosure, is subtle and therefore the two terms will be used synonymously.

It is estimated that 98% of the economically important phenotypic traits in domesticated plants are quantitative traits. These traits are classified as oligogenic or polygenic based on the perceived numbers and magnitudes of segregating genetic factors affecting the variability in expression of the phenotypic trait.

The development of ubiquitous polymorphic genetic markers that span the genome (e.g., RFLP) has made it possible for quantitative and molecular geneticists to investigate what Edwards, et al., in *Genetics* 115:113 (1987) referred to as quantitative trait loci (QTL), as well as their numbers, magnitudes and distributions. QTL include genes that control, to some degree, numerically representable phenotypic traits that are usually continuously distributed within a family of individuals as well as within a population of families of individuals. An experimental paradigm has been developed to identify and analyze QTL. This paradigm involves crossing two inbred lines, genotyping multiple marker loci and evaluating one to several quantitative phenotypic traits among the segregating progeny derived from the cross. The QTL are then identified on the basis of significant statistical associations between the genotypic values and the phenotypic variability among the segregating progeny. This experimental paradigm is ideal in that the parental lines of the $F_1$ generation have the same degree of linkage, all of the associations between the genotype and phenotype in the progeny are informative and linkage disequilibrium between the genetic loci and phenotypic traits is maximized.

Because relatively few numbers of progeny are studied, the experiments described above lack the necessary statistical power to identify QTL for most traits of economic importance in breeding populations, for example, maize, sorghum, soybean, canola, etc. Additionally, the lack of statistical power produces biased estimates of the QTL that are identified. Additional imprecision is introduced in extrapolating the identification of QTL to the progeny of genetically different parents within a breeding population.

General forms of genetic and statistical models for predicting breeding values are known in the art (Henderson, *Biometrics* 31:423 (1975)). Specific models have also been proposed for QTL identification in animal breeding (Soller & Genizi, *Biometrics* 34:47 (1978); and Fernando & Grossman, *Genet. Sel. Evol.* 21:467 (1989)) and human populations (Goldgar, *Am. J. Hum. Genet.* 47:957 (1990)). However, statistical models have not been developed for plant breeding populations. Thus, there remains a need in the art for methods that take account of and are applicable to determining QTL in commercially important plant breeding populations. The invention herein satisfies this need.

SUMMARY OF THE INVENTION

This invention provides methods of identifying quantitative trait loci in a mixed defined plant population comprising multiple plant families. The method operates by quantifying a phenotypic trait across lines sampled from the population, identifying at least one genetic marker associated with the phenotypic trait by screening a set of markers and identifying the quantitative trait loci based on the association of the phenotypic trait and the genetic marker(s).

In one embodiment, the plant population consists of diploid plants, either hybrid or inbred, preferably maize, soybean, sorghum, wheat, sunflower, and canola. In a most preferred embodiment, the plant population consists of *Zea mays*.

The phenotypic traits associated with the QTL are quantitative, meaning that, in some context, a numerical value can be ascribed to the trait. Preferred phenotypic traits include, but are not limited to, grain yield, grain moisture, grain oil, root lodging, stalk lodging, plant height, ear height, disease resistance, and insect resistance.

In a preferred embodiment, the genetic markers associated with the QTL are restriction fragment length polymorphisms (RFLP), isozyme markers, allele specific hybridization (ASH), amplified variable sequences of the plant genome, self-sustained sequence replication, simple sequence repeats (SSR), and arbitrary fragment length polymorphisms (AFLP). In another preferred embodiment, at least two genetic markers are associated with the QTL and are identified by high throughput screening.

The association of the genetic loci and the phenotypic trait is determined through specified statistical models. In a preferred embodiment, the statistical models are linear models with fixed effects and random effects. In a particularly preferred embodiment, the statistical model is a mixed effects model wherein the phenotypic trait of the progeny of one line from one family in the breeding population is evaluated in topcross combination with a tester parent.

In yet another embodiment, the identification of QTL allows for the marker assisted selection of a desired phenotypic trait in the progeny of a diploid plant breeding population selected from the group consisting of maize, soybean, sorghum, wheat, sunflower, and canola. In a particularly preferred embodiment, the plant population consists of *Zea mays*. In yet another embodiment, the phenotypic trait selected for includes, but is not limited to, yield, grain moisture, grain oil, root lodging, stalk lodging, plant height, ear height, disease resistance, and insect resistance.

In another aspect of the invention, plants selected by the methods described above are provided. In addition to plants created by selfing and sexual crosses, cloned plants are described, as are transgenic plants. The transgenic plants contain nucleic acid sequences associated with a desired QTL.

DETAILED DESCRIPTION OF THE INVENTION

I. OVERVIEW

Previously, quantitative trait loci (QTL) have been identified using a sample of segregating progeny derived from a single cross of two inbred lines, i.e., a biparental cross. The disadvantages of this method are that, for adequate statistical power, it requires a large commitment of field testing resources to be devoted to the progeny from a single cross and inferences of associations between the genetic loci and phenotype cannot be extended beyond the specific sample set of progeny. Thus, the identification of the QTL in a marker-aided selection development program for plant populations cannot be used with confidence.

Moreover, because breeding populations undergo constant selection to improve yield and resistance to pathogens, it is impractical to monitor simultaneously all relevant breeding crosses. Thus, the effects of genetic background on particular QTL are difficult to determine with conventional methods.

The present invention overcomes the need for large numbers of progeny of a single cross by using lines derived from multiple breeding crosses and phenotypic information obtained through hybrid topcrosses; technology familiar to the commercial plant breeder. Accordingly, the collection of phenotypic information does not require resources beyond those already committed for ongoing plant breeding.

The present invention overcomes the difficulties in inferring the results beyond the sample set of progeny through the acquisition of data from progeny sampled from multiple breeding crosses and the use of statistical models which account for genetic variability in different families of a breeding population. Thus inferences about QTL can be drawn across the entire breeding population. This makes it possible to predict the effects of QTL alleles on phenotypic traits in multiple genetic backgrounds.

The models of the present invention are developed using statistical methods that are relevant to the structure of plant breeding populations. The models are implemented using computing and data management software. Simulations are developed to validate the statistical models. The statistical methods are then applied to genotypic and phenotypic data collected across plant breeding populations to identify and map QTL within the genomes of the plants in those populations.

II. DEFINITIONS

Unless defined otherwise, all technical and scientific terms used herein have the meaning commonly understood by a person skilled in the art to which this invention belongs. The following references provide one of skill with a general definition of many of the terms used in this invention: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., Rieger, R., et al. (eds.), Springer Verlag (1991); and Hale & Marham, THE HARPER COLLINS DICTIONARY OF BIOLOGY (1991). Although any methods and materials similar or equivalent to those described herein can be used in the practice or testing of the present invention, preferred methods and materials are described. As used herein, the following terms have the meanings ascribed to them unless specified otherwise.

The term "association" or "associated with" in the context of this invention refers to genetic marker loci and quantitative trait loci that are in disequilibrium, i.e., the marker genotypes and trait phenotypes are found together in the progeny of a plant or plants more often than if the marker genotypes and trait phenotypes segregated separately.

The phrase "diploid plants" refers to plants that have two sets of chromosomes, typically one from each parent.

The phrase "expression cassette" refers to a nucleic acid sequence to be introduced into a transgenic plant and contains the nucleic acid sequence to be transcribed and a promoter to direct the transcription. The promoter can either be homologous, i.e., occurring naturally to direct the expression of the desired transgene or heterologous, i.e., occurring naturally to direct the expression of a nucleic acid derived from a gene other than the desired transgene. Fusion genes with heterologous promoter sequences are desirable, e.g., for regulating expression of encoded proteins. In some instances, the promoter may constitutively bind transcription factors and RNA Polymerase II. In other instances, a heterologous promoter may be desirable because it has sequences that bind transcription factors the naturally occurring promoter lacks.

The phrase "genetic marker" refers to a nucleic acid sequence present in a plant genome used to locate genetic loci that contain alleles which contribute to variability in expression of quantitative traits. Genetic markers also refer to nucleic acid sequences complementary to the genomic sequences, such as nucleic acids used as probes.

The phrase "high throughput screening" refers to assays in which the format allows large numbers of nucleic acid sequences to be screened for defined characteristics. In the context of the instant invention, high throughput screening is of nucleic acid sequences of the plant genome to identify the presence of genetic markers which co-segregate with expression of desirable phenotypic traits.

The phrase "hybrid plants" refers to plants which result from a cross between genetically divergent individuals.

The phrase "inbred plants" refers to plants derived from a cross between genetically related plants.

The term "lines" in the context of this invention refers to a family of related plants derived by self-pollinating an inbred plant.

The phrase "linkage disequilibrium" refers to a non-random association of alleles from two or more loci. It implies that a group of marker alleles or QTL alleles have been inherited together.

The term "lodging" in the context of this invention refers to the tendency of plants to fall over prior to harvest.

The phrase "marker assisted selection" refers to selection of a plant by virtue of the presence or absence of one or more genetic marker alleles. In the context of this invention, the genetic markers have been previously associated with a QTL.

The phrase "mixed defined plant population" refers to a plant population containing many different families and lines of plants. Typically, the defined plant population exhibits a quantitative variability for a phenotype that is of interest.

The phrase "multiple plant families" refers to different families of related plants within a population.

The phrase "operably linked" refers to a functional linkage between a promoter and a second sequence, wherein the promoter sequence initiates transcription of RNA corresponding to the second sequence.

The phrase "phenotypic trait" refers to the appearance or other characteristic of a plant, resulting from the interaction of its genome with the environment.

The term "progeny" refers to the descendants of a particular plant (selfcross) or pair of plants (cross-pollinated). The descendants can be, for example, of the $F_1$, the $F_2$ or any subsequent generation.

The term "promoter" refers to a nucleic acid sequence that directs expression of a coding sequence. A promoter can be constitutive, i.e., relatively independent of the stage of differentiation of the cell in which it is contained or it can be inducible, i.e., induced be specific environmental factors, such as the length of the day, the temperature, etc. or a promoter can be tissue-specific, i.e., directing the expression of the coding sequence in cells of a certain tissue type.

The phrase "quantified population phenotype" refers to a phenotypic trait present in a plant population that exhibits continuous variability and is the result of either a genetic locus interacting with the environment or multiple genetic loci possibly interacting with each other or with the environment. An example of a quantified population phenotype is plant height. Typically in the plant population, the frequency distribution of a phenotypic trait exhibits a bell curve.

The phrase "quantitative trait loci" refers to segregating genetic factors which affect the variability in expression of a phenotypic trait.

The phrase "sexually crossed" or "sexual reproduction" in the context of this invention refers to the fusion of gametes to produce seed by pollination. A "sexual cross" is pollination of one plant by another. "Selfing" is the production of seed by selfpollinization, i.e., pollen and ovule are from the same plant.

The phrase "tester parent" refers to a parent that is unrelated to and genetically different from a set of lines to which it is crossed. The cross is for purposes of evaluating differences among the lines in topcross combination. Using a tester parent in a sexual cross allows one of skill to determine the association of phenotypic trait with expression of quantitative trait loci in a hybrid combination.

The phrases "topcross combination" and "hybrid combination" refer to the processes of crossing a single tester parent to multiple lines. The purposes of producing such crosses is to evaluate the ability of the lines to produce desirable phenotypes in hybrid progeny derived from the line by the tester cross.

The phrase "transgenic plant" refers to a plant into which exogenous polynucleotides have been introduced by any means other than sexual cross or selfing. Examples of means by which this can be accomplished are described below, and include Agrobacterium-mediated transformation, biolistic methods, electroporation, in planta techniques, and the like. Such a plant containing the exogenous polynucleotides is referred to here as an $R_1$ generation transgenic plant. Transgenic plants may also arise from sexual cross or by selfing of transgenic plants into which exogenous polynucleotides have been introduced.

III. Development of Genetic and Statistical Models for Identifying and Mapping QTL in Plant Breeding Populations After genetic markers have been identified, e.g., using RFLP or other methods discussed herein, the degree of association of the genetic markers to the quantitated phenotypic trait can be used to identify and map QTL. This is done through use of statistical models.

A. Fixed Effects Model

In a fixed effects model, members of one family or full siblings are used to determine the association between genetic markers and a phenotypic trait. Soller & Genizi first proposed fixed effects models for identifying QTL using full-sibling and half-sibling population structures (Soller & Genizi, Biometrics 34:47 (1978)). Inferences about QTL effects and genomic sites derived from the association between the phenotypic trait and the genetic marker using this model are specific to the sample of lines and progeny used for the evaluation. These inferences cannot be extended to other families or progeny because the model does not view the genotypic and phenotypic data as a representative sample from a large population. The statistical model follows the form of Equation 1:

$$Y_{q(i)} = m + f_i + CX_{q(i)} + g_{q(i)} \qquad \text{Equation 1}$$

wherein $Y_{q(i)}$ is the phenotype of allele q in family i, m is the average of the phenotype in the breeding population, $f_i$ is the effect of family i, C is the combining ability of the QTL allele. C is unknown and is estimated as the difference in phenotype between homozygotes in the line per se from the line phenotype evaluated in topcrossed progeny (Beavis, W., et al., *Crop Science* 34:882 (1994)).

$X_{q(i)}$ is an indicator variable taking on values of 1 or 0 for the alleles' presence or absence in the lines from family i, and $g_{q(i)} \sim N(0, \hat{o}^2_e)$.

B. Random Effects Model

Because members of families are often genetically related and represent only a sample of all possible breeding crosses within a population, a model which would take this into account is needed.

A random effects model differs from the fixed effects model in that there are no estimated allele effects. Rather an estimate is made of the proportion of $\hat{o}^2_p$, the phenotypic variability, that can be ascribed to the variability in alleles at the QTL. Unlike the fixed effects model, it is possible to predict genotypic effects for sampled alleles at the QTL in untested progeny. Also, unlike the fixed effects model, predicted phenotypes can be extended to other related families in the breeding population. Random effects models have been prepared for fill-sibling and half-sibling family structures in human pedigrees (Goldgar, *Am. J. Hum. Genet.* 47:957 (1990)) and to general outbred populations (Xu & Atchley, *Genetics* 141:1198 (1995)). The model follows Equation 2.

$$Y_{ij} = m + C_{ij} + A_{ij} \qquad \text{Equation 2}$$

wherein $Y_{ij}$ is the phenotype of line j in family i, m is the average of the phenotype of the breeding population, $C_{ij}$ is the combining ability of the QTL, linked to the marker locus, in line j of family i and is $\sim N(0, \hat{o}^2_c)$.

$A_{ij}$ is the combining ability of all QTL, unlinked to $C_{ij}$, in line j of family i, i.e., it is the sum of the polygenic background effects that are not genetically linked to the QTL and is $\sim N(0, \hat{o}^2_a)$.

In this model, $E(Y_{ij}) = m$, $V(Y_{ij}) = \hat{o}^2_c + \hat{o}^2_e = \hat{o}^2_p$ and $Cov(Y_{ij}, Y_{ij'}) = \eth o_{i_q} \hat{o}^2_c + \eth o_{ij} \hat{o}^2_a$, wherein $\eth o_{i_q}$ is the proportion of alleles that have identity by descent (IBD) at the QTL between lines j and j' of family i. $\hat{\partial}o_{ij}$ is the proportion of alleles that are IBD at all remaining QTL between lines j and j' of family i. $\hat{\partial}o_{iq}$ is conditional on knowledge of pedigree relationships for linked marker locus genotypes.

C. Mixed Effects Model

Random effects models do not allow for tester effects. Testers are selected inbred plant lines used to evaluate lines of a family through hybrid (topcross) combination. Because testers are specifically selected, their effects on the phenotype of the progeny are fixed. Therefore, the resulting model consists of mixed random and fixed effects and follows Equation 3.

$$Y_{ijk} = m + T_k + C_{ijk} + A_{ijk} + g_{ijk} \qquad \text{Equation 3}$$

wherein $Y_{ijk}$ is the phenotypic value of the progeny of line j from family i evaluated in topcross combination with tester k, m is the average phenotype of the breeding population, $T_k$ is the fixed effect of tester k, $C_{ijk}$ is the combining ability of the alleles, at the QTL linked to the marker loci, with tester k and is $\sim N(0, \hat{\sigma}^2_c)$, $A_{ijk}$ is the combining ability of the alleles, at all QTL unlinked to the marker loci, with tester k. It is the sum of the polygenic background effects in combination with tester k, not "linked" to the QTL and is $\sim N(0, \hat{\sigma}^2_a)$, and $g_{ijk} \sim N(0, \hat{\sigma}^2_e)$.

The same inferences from the random effects, $C_{ijk}$ and $A_{ijk}$, are made as in the random effects model. The mixed effects model is an adaptation of a model first proposed by Fernando & Grossman in *Genet. Sel. Evol.* 21:467 (1989) for family structures in animal breeding populations and is usually used to describe herds and management practices.

In order to obtain estimates and predictions of effects in the model, the mixed effect model, Equation 3, is translated into incidence matrices as described in, for example, Henderson, C., *Biometrics* pp226 (1952); Henderson, C., *Biometrics* 31:423 (1975); Harville, D., *The Annals of Statistics* 4:384 (1976); Harville, D., *J. Amer. Statistical Ass'n* 72:320 (1977); and Searle, S., et al., VARIANCE COMPONENTS, John Wiley & Sons, Inc., N.Y. (1992).

IV. Quantitative Trait Loci Determined by Linkage of Phenotypic Traits with Genetic Markers A. Phenotypic Traits Determined by Multiple Genes Many of the commercially desired traits of domesticated crops are determined by multiple genes. These include such quantitative traits as plant height, grain yield, moisture and/or oil content of grain or seed, ear height (in maize), root and stalk lodging, and disease and insect resistance.

Phenotypic traits determined by multiple genes are typically continuous and follow a bell curve, with the greatest number of plants in a population exhibiting the average of the quantitative phenotypic trait. This is in comparison with single locus Mendelian genetics and its concept of dominant and recessive alleles exhibiting as one of two possible phenotypes.

In addition to the genetic element of complex traits, in breeding plant populations, environmental dynamics must be taken into account. This is done by analyzing a QTL in a variety of populations in a variety of different environments. In an alternate and preferred method, lines from multiple families within a population are crossed with tester parents, which have defined genotypes. Progeny from these crosses can be evaluated for phenotypic traits of interest in one environment or in multiple environments to determine the extent changes in the environment have on expression of the quantitative traits.

B. Genetic Markers

In the following discussion, the phrase "nucleic acid," "polynucleotide," "polynucleotide sequence" or "nucleic acid sequence" refers to deoxyribonucleotides or ribonucleotides and polymers thereof in either single- or double-stranded form. Unless specifically stated, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence of this invention also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer, et al., *Nucleic Acid Res.* 19:5081 (1991); Ohtsuka, et al., *J. Biol. Chem.* 260:2605–2608 (1985); and Rossolini, et al., *Mol. Cell. Probes* 8:91–98 (1994)). The term nucleic acid is used interchangeably with gene, cDNA, and mRNA encoded by a gene.

To identify genetic markers, labeled oligonucleotides that are complementary to the genetic marker are hybridized to the nucleic acid sequences of the individual plants. Two single-stranded nucleic acids "hybridize" when they form a double-stranded duplex. The region of double-strandedness can include the full-length of one or both of the single-stranded nucleic acids, or all of one single stranded nucleic acid and a subsequence of the other single stranded nucleic acid, or the region of double-strandedness can include a subsequence of each nucleic acid. An overview to the hybridization of nucleic acids is found in Tijssen, LABORATORY TECHNIQUES IN BIOCHEMISTRY AND MOLECULAR BIOLOGY—HYBRIDIZATION WITH NUCLEIC ACID PROBES, Part I, Chapter 2 "Overview Of Principles Of Hybridization And The Strategy Of Nucleic Acid Probe Assays," Elsevier, N.Y. (1993).

"Stringent conditions" in the context of nucleic acid hybridization are sequence dependent and are different under different environmental parameters. An extensive guide to the hybridization of nucleic acids is found in Tijssen, supra. Generally, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Highly stringent conditions are selected to be equal to the $T_m$ point for a particular probe. Nucleic acids which encode polypeptides and do not hybridize to each other under stringent conditions are still substantially identical if the polypeptides which they encode are substantially identical. This occurs, e.g., when a copy of a nucleic acid is created using the maximum codon degeneracy permitted by the genetic code.

An example of stringent hybridization conditions for hybridization of complementary nucleic acids which have more than 100 complementary residues on a filter in a Southern or northern blot is 50% formamide with heparin at 42° C., the hybridization being carried out overnight. An example of stringent wash conditions is a 0.2×SSC wash at 65° C. for 15 minutes (see, Sambrook et al., MOLECULAR CLONING—A LABORATORY MANUAL (2nd ed.) Vol. 1–3 (1989) (Sambrook, et al.) for a description of SSC buffer and wash conditions in general). Often the high stringency wash is preceded by a low stringency wash to remove background probe signal. An example of a low stringency wash for a probe with at least about 100 complementary nucleic acids is 2×SSC at 40° C. for 15 minutes. In general, a signal to noise ratio of 2× (or higher) than that observed for an unrelated probe in the particular hybridization assay indicates detection of a specific hybridization.

Genetic Variability

The ability to characterize an individual by its genome is due to the inherent variability of genetic information. Although DNA sequences which encode necessary proteins are well conserved across a species, there are regions of DNA which are non-coding or code for proteins or portions of proteins which do not have a critical function and therefore, conservation of nucleic acid sequence is not necessary. These variable regions can be identified by genetic markers. Typically, genetic markers are variable regions of a genome and the complementary oligonucleotides which bind to these regions. In some instances, the presence or absence of binding to a genetic marker identifies individuals by their unique nucleic acid sequence. In other instances, a genetic marker is found in all individuals but the individual is identified by where, in the genome, the genetic marker is located.

The major causes of genetic variability and thus, the major sources of genetic markers, are addition, deletion and point mutations, recombination events and transposable elements within the genome of individuals in a plant population.

Point mutations can be the result of inaccuracy in DNA replication. During meiosis in the creation of germ cells or in mitosis to create daughter cells, DNA polymerase "switches" bases, either transitionally (i.e., a purine for a purine and a pyrimidine for a pyrimidine) or transversionally (i.e., purine to pyrmidine and vice versa). The base switch is maintained if the exonuclease function of DNA polymerase does not correct the mismatch. At germination, or the next cell division (in clonal cells), the DNA strand with the point mutation becomes the template for a complementary strand and the base switch is incorporated into the genome.

Additions and deletions of nucleic acid sequences can be due to inaccurate recombination events. Recombination occurs when sister chromatids are aligned during cross-over events. One of the DNA strands of the chromatids break and recA protein anneals the broken strand to a complementary sequence on the sister chromatid, displacing the resident strand. If a single stranded sequence contains regions of oligonucleotide repeats, the recA protein may incorrectly use, as a template, another region of the sister chromatid which also contains the same oligonucleotide repeats. As in the case with point mutations, if the mismatched recombination is not corrected before the next cell division, one of the daughter cells will have an additional region of oligonucleotide repeats in its genome and the other will have a deletion in its genome.

Transposable elements refer to sequences of DNA which have the ability to move or to jump to new locations within a genome. Two components are required for transposition: the transposase enzyme which catalyzes transposition and the nucleotide sequences present at the end of the transposon upon which the enzyme acts. Transposons are both autonomous and non-autonomous. Autonomous transposons are those which are capable of both transposing and catalyzing the transposition of non-autonomous elements. Examples of autonomous transposons are the Ac elements and Spm transposons isolated from maize, all of which have been cloned and are well-described in the art. See, for example, U.S. Pat. No. 4,732,856 and Gierl, et al., *Plant Mol. Biol.* 13:261–266 (1989) which are incorporated by reference herein.

Autonomous transposons comprise sequences for transposase and sequences which are recognized by the transposase enzyme at the ends of the transposon (the "Ds element"). The sequences for transposase (or the transposase gene) are active independent of the end sequences, i.e., if the end sequences are eliminated, the activity of the transposase gene is preserved and the enzyme encoding element may thus be used in conjunction with a non-autonomous or Ds element to trigger transposition of the Ds element. The transposase gene is evident in the Ts101 and Ts105 elements.

Only the DNA sequences present at the ends of a non-autonomous element are required for it to be transpositionally active in the presence of the transposase gene. These ends are referred to herein as the "transposon ends" or the "Ds element." See, for example, Coupland, et al, *Proc. Nat'l Acad. Sci.* USA 86:9385 (1989), which describes the sequences necessary for transposition. The DNA sequences internal to the transposon ends are non-essential and can be comprised of sequences from virtually any source.

Restriction Fragment Length Polymorphisms (RFLP)

The net result of the mutations and changes in the DNA sequence of individuals, as described above, is that they will have different sequences in non-coding regions of the genome. When these DNA sequences are digested with restriction endonucleases which recognize specific restriction sites, the fragments will be of different lengths. The resulting fragments are restriction fragment length polymorphisms.

The phrase "restriction fragment length polymorphism" or "RFLP" refers to inherited differences in restriction enzyme sites (for example, caused by base changes in the target site), or additions or deletions in the region flanked by the restriction enzyme site that result in differences in the lengths of the fragments produced by cleavage with a relevant restriction enzyme. A point mutation will lead to either longer fragments if the mutation is within the restriction site or shorter fragments if the mutation creates a restriction site. Additions and transposable elements will lead to longer fragments and deletions will lead to shorter fragments.

An RFLP can be used as a genetic marker in the determination of segregation of alleles with quantitative phenotypes. In one embodiment of the invention, the restriction fragments are linked to specific phenotypic traits. More specifically, the presence of a particular restriction fragment is used to predict the prevalence of a specific phenotypic trait.

Amplified Variable Sequences

In one embodiment, amplified variable sequences of the plant genome and complementary nucleic acid probes are used as genetic markers. The phrase "amplified variable sequences" refers to amplified sequences of the plant genome which exhibit high nucleic acid residue variability between members of the same species. All organisms have variable genomic sequences and each organism (with the exception of a clone) has a different set of variable sequences. Once identified, the presence of a specific variable sequence can be used to predict phenotypic traits. Preferably, DNA from the plant serves as a template for amplification with primers that flank a variable sequence of DNA. The variable sequence is amplified by amplification techniques and sequenced. In vitro amplification techniques are well known. Examples of techniques sufficient to direct persons of skill through such in vitro amplification methods, including the polymerase chain reaction (PCR) the ligase chain reaction (LCR), Qâ-replicase amplification and other RNA polymerase mediated techniques (e.g., NASBA) are found in Berger & Kimmel, *Guide to Molecular Cloning Techniques*: METHODS IN ENZYMOLOGY, vol. 152, Academic Press, Inc., San Diego, Calif. (Berger); Sambrook, et al.; and CURRENT PROTOCOLS IN MOLECULAR BIOLOGY, F. M. Ausubel et al., eds., Current Protocols, a joint venture between Greene Publishing Associates, Inc. and John Wiley & Sons, Inc., (1994 Supplement) (Ausubel), as well as U.S. Pat. No. 4,683,202; PCR PROTOCOLS A GUIDE TO METHODS AND APPLICATIONS, Innis et al. eds., Academic Press Inc. San Diego, Calif. (1990) (Innis); Arnheim & Levinson (October 1, 1990) *C&EN* 36–47; Kwoh, et al., *Proc. Nat'l Acad. Sci. USA* 86:1173 (1989); Guatelli, et al., *Proc. Nat'l Acad. Sci. USA* 87:1874 (1990); Lomell, et al., *J. Clin. Chem* 35:1826 (1989); Landegren, et al., *Science* 241:1077 (1988); Van Brunt, *Biotechnology* 8:291 (1990); Wu & Wallace, *Gene* 4:560 (1989); Barringer, et al. *Gene* 89:17 (1990) and Sooknanan & Malek, *Biotechnology* 13:563 (1995). Improved methods of cloning in vitro amplified nucleic acids are described in U.S. Pat. No. 5,426,039.

Oligonucleotides for use as primers, e.g., in vitro amplification methods and for use as nucleic acid sequence probes are typically synthesized chemically according to the solid phase phosphoramidite triester method described by Beaucage & Caruthers, *Tetrahedron Lett.* 22:1859–1862 (1981).

Nucleic acid sequencing techniques are also well known. Commonly used techniques such as the dideoxy chain termination method (Sanger, et al., *Proc. Nat'l Acad. Sci. USA* 74:5463 (1977) and the Maxam and Gilbert method (Maxam & Gilbert, *Methods in Enzymology* 65:499 (1980)) can be used in practicing this invention. In addition, other nucleic acid sequencing methods, such as fluorescence-based techniques (U.S. Pat. No. 5,171,534), mass spectroscopy (U.S. Pat. No. 5,174,962) and capillary electrophoresis (U.S. Pat. No. 5,728,282) can be used.

Other amplification methods include the ligase chain reaction (LCR), the transcription-based amplification system (TAS), and the self-sustained sequence replication system.

Self-sustained Sequence Replication

In another embodiment of the invention, genetic markers are identified by self-sustained sequence replication. The phrase "self-sustained sequence replication" refers to a method of nucleic acid amplification using target nucleic acid sequences which are amplified (replicated) exponentially in vitro under isothermal conditions by using three enzymatic activities essential to retroviral replication: (1) reverse transcriptase, (2) RNase H, and (3) a DNA-dependent RNA polymerase (Guatelli, et al., *Proc. Natl. Acad. Sci. USA* 87:1874 (1990)). By mimicking the retroviral strategy of RNA replication by means of cDNA intermediates, this reaction accumulates cDNA and RNA copies of the original target.

Substantially isothermal means that the temperature may be varied over the course of an approximately one hour reaction time within the temperature range of about 37° C. to 50° C. Alternatively, one temperature may be selected to carry out the entire reaction. Self-sustained sequence replication at 45° C. is preferred.

Arbitrary Fragment Length Polymorphisms (AFLP)

In another embodiment, arbitrary fragment length polymorphisms (AFLP) are used as genetic markers (Vos, P., et al., *Nucl. Acids Res.* 23:4407 (1995)). The phrase "arbitrary fragment length polymorphism" refers to selected restriction fragments which are amplified before or after cleavage by a restriction endonuclease. The amplification step allows easier detection of specific restriction fragments rather than determining the size of all restriction fragments and comparing the sizes to a known control.

AFLP allows the detection of a large number of polymorphic markers (see, supra) and has been used for genetic mapping of plants (Becker, J., et al., *Mol. Gen. Genet.* 249:65 (1995); and Meksem, K., et al., *Mol. Gen. Genet.* 249:74 (1995)) and to distinguish among closely related bacteria species (Huys, G., et al., *Int'l J. Systematic Bacteriol.* 46:572 (1996)).

Isozyme Markers

Other embodiments include identification of isozyme markers and allele-specific hybridization. Isozymes are multiple forms of enzymes and therefore are distinct from one another in nucleic acid and/or amino acid sequences. Some isozymes are multimeric enzymes containing slightly different subunits. Other isozymes are either multimeric or monomeric but have been cleaved from the proenzyme at different sites in the amino acid sequence. For the purpose of this invention, differing isozymes at the nucleic acid sequence level are to be determined. Primers which flank a variable portion of the isozyme nucleic acid sequence are hybridized to the plant genome. The variable region is amplified and sequenced. From the sequence, the different isozymes are determined and linked to phenotypic characteristics.

Allele-Specific Hybridization (ASH)

In yet another embodiment, allele specific hybridization is used to identify genetic markers. ASH technology is based on the stable annealing of a short, single-stranded, oligonucleotide probe to a completely complementary single-strand target nucleic acid. The hybridization can then be detected from a radioactive or non-radioactive label on the probe.

ASH markers are polymorphic. For each polymorphism, two or more different ASH probes are designed to have identical DNA sequences except at the polymorphic nucleotides. Each probe will have exact homology with one allele sequence so that the complement of probes can distinguish all the alternative allele sequences. Each probe is hybridized against the target DNA. With appropriate probe design and stringency conditions, a single-base mismatch between the probe and target DNA will prevent hybridization. In this manner, only one of the alternative probes will hybridize to a target sample that is homozygous or homogeneous for an allele (an allele is defined by the DNA homology between the probe and target). Samples that are heterozygous or heterogeneous for two alleles will hybridize to both of two alternative probes.

ASH markers are used as dominant markers where the presence or absence of only one allele is determined from hybridization or lack of hybridization by only one probe. The alternative allele may be inferred from the lack of hybridization.

An ASH probe and target molecules are optionally either RNA or denatured DNA; the target molecule(s) is/are any length of nucleotides beyond the sequence that is complementary to the probe; the probe is designed to hybridize with either strand of a DNA target; the probe ranges in size to conform to variously stringent hybridization conditions, etc.

The polymerase chain reaction (PCR) allows the target sequence for ASH to be amplified from low concentrations of nucleic acid in relatively small volumes. Otherwise, the target sequence from genomic DNA is digested with a restriction endonuclease and size separated by gel electrophoresis. Hybridizations typically occur with the target sequence bound to the surface of a membrane or, as described in U.S. Pat. No. 5,468,613, the ASH probe sequence may be bound to a membrane.

In one aspect of this embodiment, utilizing nucleotide alleles and polymorphisms described here, ASH data are obtained by amplifying nucleic acid fragments (amplicons) from genomic DNA using PCR, transferring the amplicon target DNA to a membrane in a dot-blot format, hybridizing a labeled oligonucleotide probe to the amplicon target, and observing the hybridization dots by autoradiography.

Simple Sequence Repeats (SSR)

In yet another basis for providing a genetic linkage map, SSR takes advantage of high levels of di-, tri- or tetra-nucleotide tandem repeats within a genome. Dinucleotide repeats have been reported to occur in the human genome as many as 50,000 times with n varying from 10 to 60 (Jacob, et al., *Cell* 67:213 (1991)). The dinucleotide repeats have also been found in higher plants (Condit & Hubbell, *Genome* 34:66 (1991)).

Briefly, SSR data is generated by hybridizing primers to conserved regions of the plant genome which flank the SSR region. PCR is then used to amplify the dinucleotide repeats between the primers. The amplified sequences are then electrophoresed to determine the size and therefore the number of di-, tri- and tetra-nucleotide repeats.

High Throughput Screening

In a one aspect of the invention, the determination of genetic marker alleles is done by high throughput screening. In one embodiment, high throughput screening involves providing a library of genetic markers including RFLPs, AFLPs, isozymes, specific alleles and variable sequences, including SSR. Such "libraries" are then screened against plant genomes. Once the genetic marker alleles of a plant have been identified, a link between the marker allele and a desired phenotypic trait can be determined through statistical associations based on the methods described herein.

High throughput screening can be performed in many different formats. Hybridization can take place in a 96-, 324-, or a 1024-well format or in a matrix on a silicon chip or other formats as yet not developed.

In a well-based format, a dot blot apparatus is used to deposit samples of fragmented and denatured genomic DNA on a nylon or nitrocellulose membrane. After cross-linking the nucleic acid to the membrane, either through exposure to ultra-violet light if nylon membranes are used or by heat if nitrocellulose is used, the membrane is incubated with a labeled hybridization probe. The labels are incorporated into the nucleic acid probes by any of a number of means well known to those of skill in the art. The membranes are washed extensively to remove non-hybridized probes and the presence of the label on the probe is determined.

In one embodiment, a label is simultaneously incorporated during the amplification procedure in the preparation of the nucleic acid probes. Thus, for example, polymerase chain reaction (PCR) with labeled primers or labeled nucleotides provide a labeled amplification product. In another embodiment, transcription amplification using a labeled nucleotide (e.g., fluorescein-labeled UTP and/or CTP) incorporates a label into the transcribed nucleic acid probes.

Detectable labels suitable for use in the present invention include any composition detectable by spectroscopic, radioisotopic, photochemical, biochemical, immunochemical, electrical, optical or chemical means. Useful labels in the present invention include biotin for staining with labeled streptavidin conjugate, magnetic beads, fluorescent dyes (e.g., fluorescein, Texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels are detected using photographic film or scintillation counters and fluorescent markers are detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

A number of well known robotic systems have been developed for high throughput screening, particularly in a 96 well format. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art.

In addition, high throughput screening systems themselves are commercially available (see, e.g., Zymark Corp., Hopkinton, Mass; Air Technical Industries, Mentor, OH; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate or membrane in detector(s) appropriate for the assay. These configurable systems provide high throughput and rapid start up as well as a high degree of flexibility and customization. The manufacturers of such systems provide detailed protocols the various high throughput.

Solid-Phase Arrays

In one variation of the invention, solid phase arrays are adapted for the rapid and specific detection of multiple polymorphic nucleotides. Typically, a nucleic acid probe is linked to a solid support and a target nucleic acid is hybridized to the probe. Either the probe, or the target, or both, can be labeled, typically with a fluorophore. If the target is labeled, hybridization is detected by detecting bound fluorescence. If the probe is labeled, hybridization is typically detected by quenching of the label by the bound nucleic acid. If both the probe and the target are labeled, detection of hybridization is typically performed by monitoring a color shift resulting from proximity of the two bound labels.

In one embodiment, an array of probes are synthesized on a solid support. Using chip masking technologies and photoprotective chemistry, it is possible to generate ordered arrays of nucleic acid probes. These arrays, which are known, e.g., as "DNA chips," or as very large scale immobilized polymer arrays ("VLSIPS"™ arrays) can include millions of defined probe regions on a substrate having an area of about $1\ cm^2$ to several $cm^2$.

The construction and use of solid phase nucleic acid arrays to detect target nucleic acids is well described in the literature. See, Fodor, et al., Science 251:767 (1991); Sheldon, et al., Clin. Chem. 39(4):718 (1993); Kozal, et al., Nature Medicine 2(7):753 (1996) and Hubbell, U.S. Pat. No. 5,571,639. See also, Pinkel, et al., PCT/US95/16155 (WO 96/17958). In brief, a combinatorial strategy allows for the synthesis of arrays containing a large number of probes using a mininal number of synthetic steps. For instance, it is possible to synthesize and attach all possible DNA 8-mer oligonucleotides ($4^8$, or 65,536 possible combinations) using only 32 chemical synthetic steps. In general, VLSIPS™ procedures provide a method of producing $4^n$ different oligonucleotide probes on an array using only 4 n synthetic steps.

Light-directed combinatorial synthesis of oligonucleotide arrays on a glass surface is performed with automated phosphoramidite chemistry and chip masking techniques similar to photoresist technologies in the computer chip industry. Typically, a glass surface is derivatized with a silane reagent containing a functional group, e.g., a hydroxyl or amine group blocked by a photolabile protecting group. Photolysis through a photolithogaphic mask is used selectively to expose finctional groups which are then ready to react with incoming 5'-photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different oligonucleotide analogues at different locations on the array is determined by the pattern of illumination during synthesis and the order of addition of coupling reagents. Monitoring of hybridization of target nucleic acids to the array is typically performed with fluorescence microscopes or laser scanning microscopes.

In addition to being able to design, build and use probe arrays using available techniques, one of skill is also able to order custom-made arrays and arrayreading devices from manufacturers specializing in array manufacture. For example, Affymetrix in Santa Clara Calif. manufactures DNA VLSIP™ arrays.

It will be appreciated that probe design is influenced by the intended application. For example, where several probe-target interactions are to be detected in a single assay, e.g., on a single DNA chip, it is desirable to have similar melting temperatures for all of the probes. Accordingly, the length of the probes are adjusted so that the melting temperatures for all of the probes on the array are closely similar (it will be appreciated that different lengths for different probes may be needed to achieve a particular $T_m$ where different probes have different GC contents). Although melting temperature is a primary consideration in probe design, other factors are optionally used to further adjust probe construction.

Capillary Electrophoresis

In another embodiment, capillary electrophoresis is used to analyze polymorphism. This technique works best when the polymorphism is based on size, for example, RFLP and SSR. This technique is described in detail in U.S. Pat. Nos. 5,534,123 and 5,728,282. Briefly, capillary electrophoresis tubes are filled with the separation matrix. The separation matrix contains hydroxyethyl cellulose, urea and optionally formamide. The RFLP or SSR samples are loaded onto the capillary tube and electrophoresed. Because of the small amount of sample and separation matrix required by capillary electrophoresis, the run times are very short. The molecular sizes and therefore the number of nucleotides present in the nucleic acid sample is determined by techniques described herein.

In a high throughput format, many capillary tubes are placed in a capillary electrophoresis apparatus. The samples are loaded onto the tubes and electrophoresis of the samples is run simultaneously. See, Mathies & Huang, Nature 359:167 (1992). Because the separation matrix is of low viscosity, after each run, the capillary tubes can be emptied and reused.

V. Integrated Systems

Because of the great number of possible combinations present in one array, in one aspect of the invention, an integrated system such as a computer, software and data converting device is used to screen for genetic markers. The phrase "computer system" in the context of this invention refers to a system in which data entering a computer corresponds to physical objects or processes external to the computer, e.g., nucleic acid sequence hybridization and a process that, within a computer, causes a physical transformation of the input signals to different output signals. In other words, the input data, e.g., hybridization on a specific region of an array is transformed to output data, e.g., the identification of the sequence hybridized. The process within the computer is a program by which positive hybridization signals are recognized by the computer system and attributed to a region of the array. The program then determines which region of the array the hybridized nucleic acid sequences are located and the specific nucleic acid sequences which hybridize to the probe.

VI. Marker Assisted Selection in Plants

A primary motivation for development of molecular markers in crop species is the potential for increased efficiency in plant breeding through marker assisted selection (MAS). After QTL have been identified through the statistical models described above, the corresponding genetic marker alleles can be used to identify plants that contain the desired genotype at multiple loci and would be expected to transfer the desired genotype along with the desired phenotype to its progeny.

The presence and/or absence of a particular genetic marker allele in the genome of a plant exhibiting a preferred phenotypic trait is made by any method listed above, e.g., RFLP, AFLP, SSR, amplification of variable sequences, and ASH. If the nucleic acids from the plant hybridizes to a probe specific for a desired genetic marker, the plant can be selfed to create a true breeding line with the same genome or it can be crossed with a plant with the same QTL or with other desired characteristics to create a sexually crossed $F_1$ generation.

"Positional gene cloning" uses the proximity of a genetic marker to physically define a cloned chromosomal fragment that is linked to a QTL identified using the statistical methods herein. Clones of linked nucleic acids have a variety of uses, including as genetic markers for identification of linked QTLs in subsequent marker assisted selection (MAS) protocols, and to improve desired properties in recombinant plants where expression of the cloned sequences in a transgenic plant affects an identified trait. Common linked sequences which are desirably cloned include open reading frames, e.g., encoding nucleic acids or proteins which provide a molecular basis for an observed QTL. If markers are proximal to the open reading frame, they may hybridize to a given DNA clone, thereby identifying a clone on which the open reading frame is located. If flanking markers are more distant, a fragment containing the open reading frame may be identified by constructing a contig of overlapping clones.

In certain applications it is advantageous to make or clone large nucleic acids to identify nucleic acids more distantly linked to a given marker, or isolate nucleic acids linked to or responsible for QTLs as identified herein. It will be appreciated that a nucleic acid genetically linked to a polymorphic nucleotides optionally resides up to about 50 centimorgans from the polymorphic nucleic acid, although the precise distance will vary depending on the cross-over frequency of the particular chromosomal region. Typical distances from a polymorphic nucleotide are in the range of 1–50 centimorgans, for example, often less than 1 centimorgan, less than about 1–5 centimorgans, about 1–5, 1, 5, 10, 15, 20, 25, 30, 35, 40, 45 or 50 centimorgans, etc.

Many methods of making large recombinant RNA and DNA nucleic acids, including recombinant plasmids, recombinant lambda phage, cosmids, yeast artificial chromosomes (YACs), P1 artificial chromosomes, Bacterial Artificial Chromosomes (BACs), and the like are known. A general introduction to YACs, BACs, PACs and MACs as artificial chromosomes is described in Monaco & Larin, *Trends Biotechnol.* 12:280–286 (1994). Examples of appropriate cloning techniques for making large nucleic acids, and instructions sufficient to direct persons of skill through many cloning exercises are also found in Berger, Sambrook, and Ausubel, all supra.

In one aspect, nucleic acids hybridizing to the genetic markers linked to QTLs identified by the above methods are cloned into large nucleic acids such as YACs, or are detected in YAC genomic libraries cloned from the crop of choice. The construction of YACs and YAC libraries is known. See, Berger, supra, and Burke, et al., *Science* 236:806–812 (1987). Gridded libraries of YACs are described in Anand, et al., *Nucleic Acids Res.* 17:3425–3433(1989), Anand, et al., *Nucleic Acids Res.* 18:1951–1956 (1990) and Riley, *Nucleic Acids Res.* 18(10): 2887–2890 (1990) and the references therein describe cloning of YACs and related technologies. YAC libraries containing large fragments of soybean DNA have been constructed. See, Funke & Kolchinsky, CRC Press, Boca Raton, Fla. pp. 125–308 (1994); Marek & Shoemaker, *Soybean Genet. Newsl.* 23:126–129 (1996); Danish, et al, *Soybean Genet. Newsl.* 24:196–198 (1997). YAC libraries for many other commercially important crops are available, or can be constructed using known techniques. See also, Ausubel, chapter 13 for a description of procedures for making YAC libraries.

Similarly, cosmids or other molecular vectors such as BAC and P1 constructs are also useful for isolating or cloning nucleic acids linked to genetic markers. Cosmid cloning is also known. See, e.g., Ausubel, chapter 1.10.11 (supplement 13) and the references therein. See also, Ish-Horowitz & Burke, *Nucleic Acids Res.* 9:2989–2998 (1981); Murray, LAMBDA II (Hendrix et al., eds.) pp395–432, Cold Spring Harbor Laboratory, N.Y. (1983); Frischauf, et al., *J. Mol. Biol.* 170:827–842 (1983); and Dunn & Blattner, *Nucleic Acids Res.* 15:2677–2698 (1987), and the references cited therein. Construction of BAC and P1 libraries is known; see, e.g., Ashworth, et al., *Anal. Biochem.* 224(2):564–571 (1995); Wang, et al., *Genomics* 24(3):527–534 (1994); Kim, et al., *Genomics* 22(2):336–9 (1994); Rouquier, et al., *Anal. Biochem.* 217(2):205–9 (1994 Shizuya, et al., *Proc. Nat'l Acad. Sci. USA* 89(18):8794–7 (1992); Kim, et al., *Genomics* 22(2):336–9 (1994); Woo, et al., *Nucleic Acids Res.* 22(23):4922–31 (1994); Wang, et al., *Plant* 3:525–33 (1995); Cai, *Genomics* 29(2): 413–25 (1995); Schmitt, et al., *Genomics* 1996 33(1):9–20 (1996); Kim, et al., *Genomics* 34(2):213–8 (1996); Kim, et al., *Proc. Nat'l Acad. Sci. USA* 13:6297–301 (1996); Pusch, et al, *Gene* 183(1–2):29–33 (1996) and Wang, et al., *Genome Res.* 6(7):612–9 (1996). Improved methods of in vitro amplification to amplify large nucleic acids linked to the polymorphic nucleic acids herein are summarized in Cheng, et al., *Nature* 369:684–685 (1994) and the references therein.

In addition, any of the cloning or amplification strategies described herein are useful for creating contigs of overlapping clones, thereby providing overlapping nucleic acids which show the physical relationship at the molecular level for genetically linked nucleic acids. A common example of this strategy is found in whole organism sequencing projects, in which overlapping clones are sequenced to provide the entire sequence of a chromosome. In this procedure, a library of the organism's cDNA or genomic DNA is made according to standard procedures described, e.g., in the references above. Individual clones are isolated and sequenced, and overlapping sequence information is ordered to provide the sequence of the organism. See also, Tomb, et al., *Nature* 388:539–547 (1997) describing the whole genome random sequencing and assembly of the complete genomic sequence of Helicobacterpylori; Fleischmann, et al., *Science* 269:496–512 (1995) describing whole genome random sequencing and assembly of the complete Haemophilus influenzae genome; Fraser, et al., *Science* 270:397–403 (1995) describing whole genome random sequencing and assembly of the complete Mycoplasma genitalium genome and Bult, et al., *Science* 273:1058–1073 (1996) describing whole genome random sequencing and assembly of the complete Methanococcusjannaschii genome. Recently, Hagiwara and Curtis, *Nucleic Acids Res.* 24(12):2460–2461 (1996) developed a "long distance sequencer" PCR protocol for generating overlapping nucleic acids from very large clones to facilitate sequencing, and methods of amplifying and tagging the overlapping nucleic acids into suitable sequencing templates. The methods can be used in conjunction with shotgun sequencing techniques to improve the efficiency of shotgun methods typically used in whole organism sequencing projects. As applied to the present invention, the techniques are useful for identifying and sequencing genomic nucleic acids genetically linked to the QTLs as well as "candidate" genes responsible for QTL expression as identified by the methods herein.

In another embodiment, $F_1$ clonal plants can be grown from cells of the selected plant. In yet another embodiment, the allelic sequences that comprise a QTL can be cloned and inserted into a transgenic plant. Methods of creating transgenic plants are well known in the art and are described in brief below.

VII. Transgenic Plants

A. Making Transgenic Plants

Nucleic acids derived from those linked to a QTL identified by the statistical methods herein are introduced into plant cells, either in culture or in organs of a plant, e.g., leaves, stems, fruit, seed, etc. The expression of natural or synthetic nucleic acids can be achieved by operably linking a nucleic acid of interest to a promoter, incorporating the construct into an expression vector, and introducing the vector into a suitable host cell.

Typical vectors contain transcription and translation terminators, transcription and translation initiation sequences, and promoters useful for regulation of the expression of the particular nucleic acid. The vectors optionally comprise generic expression cassettes containing promoter, gene, and terminator sequences, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman & Smith, *Gene* 8:81 (1979); Roberts, et al., *Nature*, 328:731 (1987); Schneider, et al., *Protein Expr. Purif.* 6435:10 (1995); Berger & Kimmel; Sambrook and Ausubel.

B. Cloning of QTL Allelic Sequences into Bacterial Hosts

Bacterial cells can be used to increase the number of plasmids containing the DNA constructs of this invention. The bacteria are grown to log phase and the plasmids within the bacteria are isolated by a variety of methods known in the art (see, for instance, Sambrook). In addition, a plethora of kits are commercially available for the purification of plasmids from bacteria. For their proper use, follow the manufacturer's instructions (see, for example, EasyPrep™, FlexiPrep™, both from Pharmacia Biotech; StrataClean™, from Stratagene; and, QIAexpress™ Expression System, Qiagen). The isolated and purified plasmids can then be further manipulated to produce other plasmids, used to transfect plant cells or incorporated into Agrobacterium tumefaciens to infect plants.

The in vitro delivery of nucleic acids into bacterial hosts can be to any cell grown in culture. Contact between the cells and the genetically engineered nucleic acid constructs, when carried out in vitro, takes place in a biologically compatible medium. The concentration of nucleic acid varies widely depending on the particular application, but is generally between about 1 iM and about 10 mM. Treatruent of the cells with the nucleic acid is generally carried out at physiological temperatures (about 37° C.) for periods of time of from about 1 to 48 hours, but preferably of from about 2 to 4 hours.

Alternatively, the nucleic acid operably linked to the promoter to form a fusion gene can be expressed in bacteria such as *E. coli* and its gene product isolated and purified. There are several well-known methods of introducing nucleic acids into bacterial cells, any of which may be used in the present invention. These include: fusion of the recipient cells with bacterial protoplasts containing the DNA, electroporation, projectile bombardment, and infection with viral vectors, etc.

C. Transfecting Plant Cells

Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising, et al., *Ann. Rev. Genet.* 22:421–477 (1988). A DNA sequence, coding for the desired polypeptide, for example, a cDNA sequence encoding a full length protein, will preferably be combined with transcriptional and translational initiation regulatory sequences which will direct the transcription of the sequence from the gene.

Promoters can be identified by analyzing the 5' sequences upstream of the coding sequence of an allele associated with a QTL. Sequences characteristic of promoter sequences can be used to identify the promoter. Sequences controlling eukaryotic gene expression have been extensively studied. For instance, promoter sequence elements include the TATA box consensus sequence (TATAAT), which is usually 20 to 30 base pairs upstream of the transcription start site. In most instances the TATA box is required for accurate transcription initiation. In plants, further upstream from the TATA box, at positions −80 to −100, there is typically a promoter element with a series of adenines surrounding the trinucleotide G (or T) N G. J. Messing, et al., in GENETIC ENGINEERING IN PLANTS, pp. 221–227 (Kosage, Meredith and Hollaender, eds. (1983)).

A number of methods are known to those of skill in the art for identifying and characterizing promoter regions in plant genomic DNA (see, e.g., Jordano, et al., *Plant Cell* 1:855–866 (1989); Bustos, et al., *Plant Cell* 1:839–854 (1989); Green, et al., EMBO J. 7:4035–4044 (1988); Meier, et al., *Plant Cell* 3:309–316 (1991); and Zhang, et al., *Plant Physiology* 110:1069–1079 (1996)).

In construction of recombinant expression cassettes of the invention, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35 S transcription initiation region, the ubiquitin promoter, the 1'- or 2'-promoter derived from T-DNA of *Agrobacterium tumafaciens*, and other transcription initiation regions from various plant genes known to those of skill.

Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers. As noted above, the tissue specific E8 promoter from tomato is particularly useful for directing gene expression so that a desired gene product is located in fruits. Other suitable promoters include those from genes encoding embryonic storage proteins. Examples of environmental conditions that may affect transcription by inducible promoters include anaerobic conditions, elevated temperature, or the presence of light.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or glufosinate.

Introduction of the Nucleic Acids into Plant Cells

The DNA constructs of the invention are introduced into plant cells, either in culture or in the organs of a plant by a variety of conventional techniques. For example, the DNA construct can be introduced directly into the genomic DNA of the plant cell using techniques such as electroporation and microinjection of plant cell protoplasts, or the DNA constructs can be introduced directly to plant cells using ballistic methods, such as DNA particle bombardment. Alternatively, the DNA constructs are combined with suitable T-DNA flanking regions and introduced into a conventional *Agrobacterium tumefaciens* host vector. The virulence functions of the *Agrobacterium tumefaciens* host directs the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski, et al., *EMBO J.* 3:2717 (1984). Electroporation techniques are described in Fromm, et al., *Proc. Nat'l Acad. Sci. USA* 82:5824 (1985). Ballistic transformation techniques are described in Klein, et al., *Nature* 327:70–73 (1987).

*Agrobacterium tumefaciens*-mediated transformation techniques, including disarming and use of binary vectors, are also well described in the scientific literature. See, for example Horsch, et al., *Science* 233:496–498 (1984), and Fraley, et al., *Proc. Nat'l Acad. Sci. USA* 80:4803 (1983). Agrobacterium-mediated transformation is a preferred method of transformation of dicots.

Generation of Transgenic Plants

Transformed plant cells which are derived by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., PROTOPLASTS ISOLATION AND CULTURE, HANDBOOK OF PLANT CELL CULTURE, pp. 124–176, Macmillian Publishing Company, N. Y., (1983); and Binding, REGENERATION OF PLANTS, PLANT PROTOPLASTS, pp. 21–73, CRC Press, Boca Raton, (1985). Regeneration can also be obtained from plant callus, explants, somatic embryos (Dandekar, et al., *J. Tissue Cult. Meth.* 12:145 (1989); McGranahan, et al., *Plant Cell Rep.* 8:512 (1990)), organs, or parts thereof. Such regeneration techniques are described generally in Klee, et al., *Ann. Rev. of Plant Phys.* 38:467–486 (1987).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

It is understood that the embodiments described herein are for illustrative purposes only and that various modifications or changes in light thereof will be suggested to persons skilled in the art and are to be included within the spirit and purview of this application and the scope of the appended claims. All publications, patents, and patent applications cited herein are hereby incorporated by reference for all purposes.

What is claimed is:

1. A method of identifying quantitative trait loci in a mixed defined plant population comprising multiple plant families, the method comprising:

i) providing a mixed defined plant population, which mixed population comprises a plurality of progeny from different families or lines of plants;

ii) quantifying a phenotypic trait among progeny sampled from different families or lines of plants of the mixed population, thereby providing a quantitated phenotypic trait;

iii) identifying at least one genetic marker associated with the distribution of the phenotypic trait by evaluating a set of markers for associations with the quantitated phenotypic trait, wherein the association is evaluated according to a statistical model, which statistical model is a fixed effects model, a random effects model, or a mixed effects model; and iv) identifying the quantitative trait loci based on the association of the quantitated phenotypic trait and genetic marker.

2. The method of claim 1, comprising, quantifying a phenotypic trait among progeny sampled from a mixed defined plant population consisting of diploid plants.

3. The method of claim 1, comprising, quantifying a phenotypic trait among progeny sampled from a mixed defined plant population consisting of inbred plants.

4. The method of claim 1, comprising, quantifying a phenotypic trait among progeny sampled from a mixed defined plant population consisting of hybrid plants.

5. The method of claim 1, wherein the phenotypic trait of the progeny of at least one line from at least one family in the mixed defined plant population is evaluated in topcross combination with at least one tester parent.

6. The method of claim 1, wherein the plant population is selected from maize, soybean, sorghum, wheat, sunflower, or canola.

7. The method of claim 6, wherein the plant population is maize.

8. The method of claim 7, wherein the plant population consists of the species *Zea mays*.

9. The method of claim 1, wherein the phenotypic trait is selected from yield, grain moisture, grain oil, root lodging, stalk lodging, plant height, ear height, disease resistance, or insect resistance.

10. The method of claim 1, wherein at least two genetic markers are identified in association with the quantitated phenotypic trait.

11. The method of claim 1, wherein genotyping of genetic markers used for association with the phenotypic trait is done by high throughput screening.

12. The method of claim 1, wherein the genetic markers are selected from the group consisting of restriction fragment length polymorphisms (RFLP), isozyme markers, allele specific hybridization (ASH), amplified variable sequences of plant genome, self-sustained sequence replication, simple sequence repeat (SSR), and arbitrary fragment length polymorphisms (AFLP).

13. The method of claim 12, wherein the genetic markers are defined by allele specific hybridization.

14. The method of claim 1, wherein the statistical model comprises parameters with fixed effects, random effects, or mixed effects for QTL and family backgrounds.

15. The method of claim 1, comprising evaluating the association of the phenotypic trait and the genetic markers by a fixed effects model according to Equation 1.

16. The method of claim 1, comprising evaluating the association of the phenotypic trait and the genetic markers by a random effects model according to Equation 2.

17. The method of claim 1, comprising evaluating the association of the phenotypic trait and the genetic markers by a mixed effects model according to Equation 3.

18. The method of claim 1, further comprising selecting for a desired phenotypic trait in progeny of a plant breeding population.

19. The method of claim 18, wherein the plant population consists of diploid plants.

20. The method of claim 18, wherein the plant population consists of hybrid plants.

21. The method of claim 18, wherein the plant population consists of inbred plants.

22. The method of claim 18, wherein the plant population is maize, soybean, sorghum, wheat, sunflower, or canola.

23. The method of claim 22, wherein the plant population is maize.

24. The method of claim 23, wherein the plant population consists of the species *Zea mays*.

25. The method of claim 18, wherein the phenotypic trait is yield, grain moisture, grain oil, root lodging, stalk lodging, plant height, ear height, disease resistance, or insect resistance.

26. The method of claim 18, comprising identifying at least two genetic markers.

27. The method of claim 18, wherein genotypes of the identified makers is determined by high throughput screening.

28. The method of claim 18, wherein the statistical model comprises parameters with fixed effects, random effects, or mixed effects for QTL and family backgrounds.

29. The method of claim 18, comprising evaluating the association of the phenotypic trait and the genetic markers by a fixed effects model according to Equation 1.

30. The method of claim 18, comprising evaluating the association of the phenotypic trait and the genetic markers by a random effects model according to Equation 2.

31. The method of claim 18, comprising evaluating the association of the phenotypic trait and the genetic markers by a mixed effects model according to Equation 3.

32. The method of claim 18, comprising selecting for the quantitative trait loci identified in step (iv) by marker assisted selection.

33. A method of selecting plants with a desired phenotype by marker assisted selection of genetic markers associated with at least one quantitative trait loci identified by the method of claim 1.

34. A plant selected by the method of claim 18.

* * * * *